United States Patent [19]
DeWitt

[11] Patent Number: 5,419,344
[45] Date of Patent: May 30, 1995

[54] RAZOR BUMP ELECTROLYSIS

[75] Inventor: Thomas L. DeWitt, 3555 Warburton Ave. Bldg. 9 Apt. 139, Santa Clara, Calif. 95051

[73] Assignee: Thomas Lee DeWitt, Santa Clara, Calif.

[21] Appl. No.: 234,545

[22] Filed: Apr. 28, 1994

[51] Int. Cl.$^6$ ............................................. A61B 17/41
[52] U.S. Cl. ...................................... 128/898; 606/36
[58] Field of Search ................................... 606/41–44, 606/36; 128/897, 898

[56] References Cited

U.S. PATENT DOCUMENTS

| | | | |
|---|---|---|---|
| 3,981,681 | 9/1976 | de la Guardia | 8/161 |
| 4,219,548 | 8/1980 | Reller | 424/234 |
| 4,228,163 | 10/1980 | Bliss | 424/240 |
| 4,364,940 | 12/1982 | Neiss et al. | 424/230 |
| 4,525,344 | 6/1985 | Tutsky | 424/73 |
| 4,665,063 | 5/1987 | Bar-Shalom | 514/164 |
| 4,775,530 | 10/1988 | Perricone | 424/73 |
| 4,846,179 | 7/1989 | O'Connor . | |
| 4,940,466 | 7/1990 | Paduano et al. | 606/44 X |
| 5,026,369 | 6/1991 | Cole | 606/36 |
| 5,034,221 | 7/1991 | Rosen et al. | 424/73 |
| 5,221,280 | 6/1993 | Gross et al. | 606/43 X |

Primary Examiner—Lee S. Cohen
Assistant Examiner—Samuel Gilbert

[57] ABSTRACT

An electro-medical method for the treatment of pseudo-folliculitis barbae ("razor bumps") through the use of electrolysis. The current invention suggests treating only the visible causative follicles of the above condition, and at least to the point of the hair follicle becoming straight and thin enough to prevent the hair from reentering into the skin. Generally, it takes two or more treatments to completely kill a curly coarse hair follicle. With each treatment the hair would regrow straighter and thinner, preventing the recurrence of the disease. It is possible to prevent the recurrence of the above condition with only one treatment; therefore a patient would still be able to regrow hairs in the beard area. During the process of the present invention a patient would shave a number of days prior to treatment (three to seven days), to allow the hairs to become ingrown into the skin adjacent the follicle. An electrologist would then treat the causative follicles relieving a patient from pain and discomfort. During electrolysis treatment, current is directed into the soft moist tissue surrounding the hair follicle. The current reaches the salt water content within the hair follicle, and this results in a decomposition process. Significant or permanent damage to the normal tissue or other harmful results is avoided by the utilization of a low discharge power and a short duration or application. If needed, an injectible form of cortizone (such as Kenalog) could be used at the very end of all treatments to reduce the size of any preexisting scar tissue caused by infection or ingrown hairs.

16 Claims, 1 Drawing Sheet

RAZOR BUMP ELECTROLYSIS

FIELD OF INVENTION

The present invention relates to the disorder known as pseudofolliculitis barbae, and more particularly to an electro-medical method for treatment and prevention of pseudofolliculitis barbae through the process of electrolysis.

BACKGROUND OF INVENTION

In 1875 Doctor Charles E. Michael, an ophthalmologist, of St. Louis, Mo., developed a technique using electric current generated by a battery cell that controlled permanent hair removal. This marked the beginning of what is known as electrolysis.

For a great many years, electrolysis used only a direct current, which produces a chemical reaction of sodium hydroxide, or lye. The sodium hydroxide is caustic and literally eats away at the hair.

Direct current electrolysis causes a low rate of regrowth, however it takes a substantial period of time (one to three minutes) for each hair follicle. Therefore, considering the wages of an electrologist, direct current electrolysis becomes quite expensive. Also, direct current electrolysis is somewhat painful to the patient.

In recent years, a new electrolysis technique, called "thermolysis" became prevalent. Thermolysis used a probe in the same manner as direct current electrolysis used a probe. However, with thermolysis, instead of direct current, a high frequency sinusoidal voltage is injected into the follicle. The radio frequency tends to physically cook the follicle.

Thermolysis has a primary advantage in that it is exceedingly fast and can be even faster than a tenth of a second for high intensity burst of radio frequency energy.

The heating pattern of thermolysis is narrow and has a less permanent effect when treating a heavy or curly hair only once. It is to be kept in mind that any portion of the hair follicle that has not been destroyed will be capable of regrowing.

Most recently, a new technique came to pass which is frequently called the "blend" technique. This blend technique combines the direct current technique with the radio frequency technique. The radio frequency technique causes heat in the follicle which increases the rate of chemical reaction for the direct current. The heat also tends to open the tissue allowing the lye to penetrate the tissue much more quickly. The result is all the reliability and low regrowth rates of the direct current technique has been obtained within a substantially shorter period of time.

Normal treatment time for the blend technique is about twenty to thirty seconds. This is considerably longer than the thermolysis technique by itself, but also substantially shorter than the direct current electrolysis by itself. Also, using the blend technique, uniform reliability throughout all different hair types is obtained.

It should be kept in mind that the time variation of any technique has to do with the pain threshold of a particular patient. If the patient can undergo a higher level of pain, he can then have the hair removed more quickly than another patient who is more sensitive to pain. The time variation of the present invention has to do with the hair removal rate verses the amount of regrowth of hair from a treated follicle.

The current invention suggests the use of the blend technique to treat pseudofolliculitis barbae but is not limited to the direct current and thermolysis methods.

Pseudofolliculitis barbae is the clinical name given to the condition commonly referred to as "razor bumps." Generally, the condition describes the ingrowth of emerged facial hairs back into the skin at a location closely adjacent to the follicle from which the hair emerged. This penetration back into the skin causes an antigenic, foreign-body reaction at the point of penetration, resulting in lesions consisting of firm papules and pustules in which the ingrowing hair can become buried. Additional infections can become superimposed on this basic state, augmenting the inflammatory reaction. As a consequence, shaving becomes problematic and painful.

From a purely mechanical point of view, pseudofolliculitis barbae comes about by virtue of strongly curved facial hairs. For this reason, the condition tends to have a greater incidence in males of the Negro race. These curved facial hairs emerge closely parallel to the skin and, owing to their curvature, are biased toward reentry into the skin. Because of their emergence so close to the skin surface, these hairs often are not closely cut at their point of emergence during shaving. In practice, shaving operates to aggravate the condition because shaving serves to obliquely cut the biased hair, above the skin surface, leaving a relatively sharp point at the tip which facilitates skin penetration. As such, the act of shaving is at least a partial cause of the condition itself.

Between one shave and the next, the point or tip of the hair ingrows into the skin bringing about the reaction and condition set forth above.

Those suggestions which exist for dealing with the condition of pseudofolliculitis barbae involve both treatment and prevention. In terms of treatment, it is necessary to treat the causative follicles; and for this reason, the present invention suggests electrolysis. The effects of the condition can then be permanently cured.

BACKGROUND—PRIOR ART

Prevention of pseudofolliculitis barbae has proven difficult. In theory, frequent shaving which cuts emerging facial hairs exactly at the skin surface would eliminate the condition by regularly removing the hairs before they have an opportunity to grow and reenter the skin. The difficulty therein is that cutting facial hairs precisely at skin level is difficult and frequent shaving will bring with it the condition of sharp hair ends which might actually hasten the onset of the condition. Some effects of cut facial hair at the skin level have involved the stretching of the skin which actually results in the cutting of the hairs below the skin level. This can result in an intrafollicular ingrown hair in which the sharp tip curved hair, instead of emerging from the follicle, penetrates the follicular wall, bringing about the same or similar foreign-body reation as would occur when a hair normally emerges from the follicle, but then reenters the skin.

The use of depilatory compositions has been suggested for the prevention of pseudofolliculitis barbae. For some, this can be effective in achieving the non-cutting removal of the hairs before they can reenter the skin. However, for others, the depilatory itself can become an irritant.

Also suggested were compositions which soften the facial hair to inhibit their ability to penetrate the skin.

However, most of these compositions bring about skin irritations or other dermatological side effects when used with a frequency required to ensure prevention of the condition.

Prior art known to the inventors concerning the subject of pseudofolliculitis barbae includes U.S. Pat. Nos. 3,981,681; 4,228,163; 4,525,344; 4,775,530; and 5,034,221. None of these references teach or suggest the use of electrolysis.

Also known to the inventors herein is U.S. Pat. No. 4,219,548 (1980) to Reller, entitled Topical Anti-inflammatory Composition; U.S. Pat. No. 4,364,940 (1982) to Neiss, entitled Compositions for Treating Acne; and U.S. Pat. No. 4,665,063 (1987) to Bar-Shalom, entitled Method of Treating Acne. Each of these references deal with the treatment of ache. Acne, however, differs materially from pseudofolliculitis barbae. More particularly, acne is an inflammatory process involving the sebaceous or oil glands of the skin and most notably, the skin of the face.

OBJECTS AND ADVANTAGES OF INVENTION

There are several reasons why prior art has not considered the use of electrolysis to treat pseudofolliculitis barbae. To begin, all hair follicles throughout the beard area are not the same. Some may be straight and clean, while others are distorted, twisted, curved, spiraled and even "L" or "U" shaped. It is almost impossible for anyone to determine which follicles potentially cause pseudofolliculitis barbae prior to the onset of the condition. Furthermore, an attempt to treat all of the follicles would prove to be very costly and prolong treatment. Deep, coarse, curly hairs are the main cause of pseudofolliculitis barbae and cannot always be cauterized or permanently eliminated in just one treatment.

For these reasons, the current invention suggests treating only the visible causative follicles and, at least, to the point of the follicle becoming straight and thin enough to prevent the hair from reentering the skin. During a series of treatments, an individual would shave prior to visiting an electrologist, allowing enough time for the onset of the disease. An electrologist would then treat only the causative follicles, relieving an individual from pain and discomfort. This process would be repeated until the condition reaches a controlled state. An individual would be encouraged to shave with clippers or trimmers since many straight razors cut hairs below the skin resulting in intrafollicular ingrown hairs.

Quite surprisingly, after a long history of extensive experimentation, study and evaluation of many topical applications, it has now been discovered that pseudofolliculitis barbae can be effectively and permanently treated by the use of electrolysis, without any significant adverse effects. The described treatment is obviously advantageous over depilatory compositions, special designed razors, and other conventional topical agents, because this is a permanent method of treatment. In addition to the treatment of pseudofolliculitis barbae, it is intended that the present invention will also provide a method which will provide relief from pain caused by the disease after shaving the skin of all racial types.

SUMMARY OF THE INVENTION

One object of the present invention is to provide a method for treating and preventing, or, at the least, to minimize the occurrence and severity of pseudofolliculitis barbae.

Another object of the invention is to provide a method for treating and preventing pseudofolliculitis barbae with a method that is essentially devoid of harmful or uncomfortable side effects.

It is therefore an object of the present invention to provide an efficient and fairly painless electrolysis method for removing hairs causing pseudofolliculitis barbae.

A further object of the present invention resides in the provision of an electrolysis process of the characters referred to above that is easy to use, reliable, and safe.

These and other objects are achieved by virtue of the discovery that the use of electrolysis to causative hair follicles of the facial beard areas is effective in preventing or minimizing the occurrence of pseudofolliculitis barbae and in alleviating such conditions where it is preexisting.

Other objects and advantages of the present invention will become apparent from a study of the following description and the accompanying drawings which are merely illustrative of such invention.

DESCRIPTION OF INVENTION

With further reference to the drawings, the present invention to treat pseudofolliculitis barbae by the use of electrolysis is illustrated therein.

Figure 1:
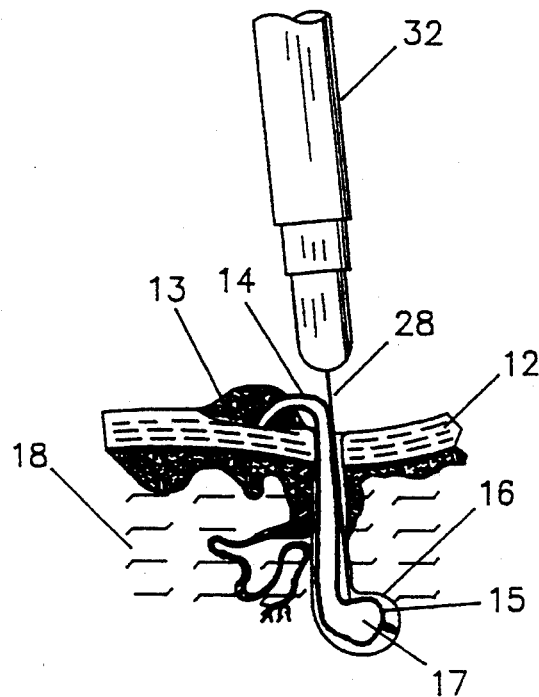
FIG. 1 shows a patient's skin and hair structure along with an invasive electrolysis hair connector.

FIG. 1 shows a patient's skin and hair structure along with an invasive electrolysis instrument. As shown in the drawings, the patient's skin surface is indicated by the number 12. Extending upward through the patient's skin surface (12) is a distorted hair shaft (14). The tip of the hair shaft (14) is ingrown inside the skin surface (12). This ingrown hair has caused a firm pustule or papule (13). The basic hair shaft (14) extends downwardly through the skin of the patient and is anchored or set below the skin surface (12). The basic hair structure lying below the skin surface is referred to as the hair follicle and is indicated in the drawings generally by the number 16. Inserted into the hair follicle (16) is an electrical hair connector (28) in the form of a probe or needle which includes an insulated holding portion (32) to be held by an electrologist. The hair connector (28) is to be inserted within the hair follicle (16) directly adjacent to the hair shaft (14). The tip of the hair connector (28) is to be located directly adjacent to a bulb (15) of the hair shaft (14). The bulb (15) includes a papilla (17).

Surrounding hair shaft (14) below the surface of the skin (12) is what is referred to as soft moist tissue, and this is referred to by the number 18. As will be further understood from subsequent portions of this disclosure, the soft moist tissue (18) acts as a conductor of electrical current in the electrolysis process.

Figure 2:
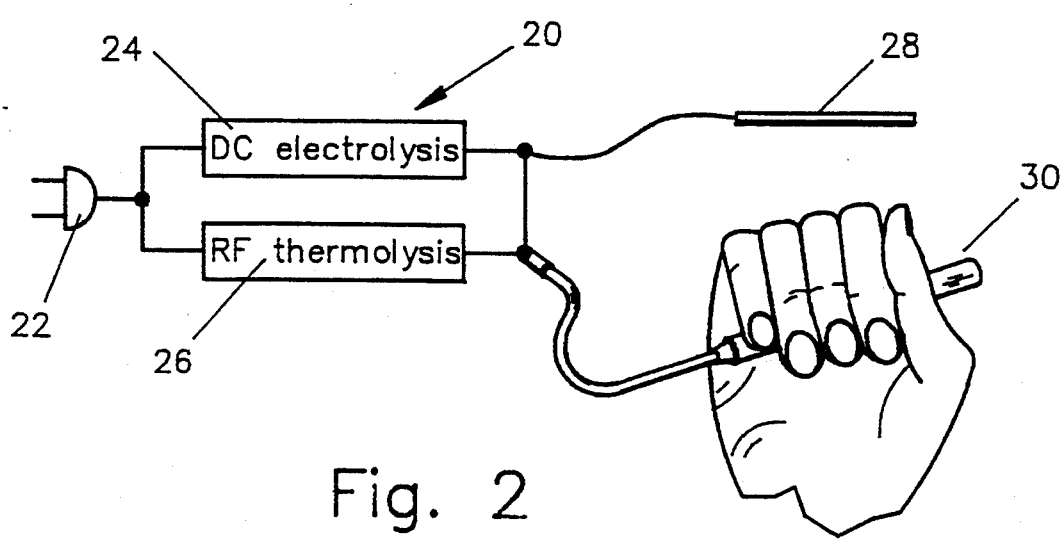
FIG. 2 shows a patient grounded to the block circuitry of an electrolysis epilator which could be used during the present invention.

FIG. 2 shows the block circuitry of an electrolysis epilator which could be used during the present invention. To carry out the present process, it is required that there be a current source, and in the drawings this current source is indicated generally by the number 20. The device forming the current source (20) is a conventional current producing electrolysis device. The electrical circuitry is to be connected to a source of electricity (not shown) through the use of a conventional electrical plug (22). The electrical plug (22) supplies electrical energy to a direct current circuit (24) and also to a radio frequency thermolysis circuit (26). Both circuits (24) and (26) feed directly to the electrical hair connecting probe (28). This electrolysis machine includes two completely separate circuits. One circuit uses direct current, while the other circuit emits a radio frequency. The amperage of the direct current is controlled so as to not exceed a certain pre-established value. For example, a typical current device of this type is U.S. Pat. No. 4,598,709 invented by Margaret M. and David C. Smith.

In any event, the current source includes a ground device (30) in the form of a hand-held conductor that is coupled to the current source (20). The ground device (30) is to be held by a patient.

Now turning to the particular process of the present invention in the hair removal process.

OPERATION OF INVENTION

The current invention suggests treating only the visible causative follicles of the above condition, and at least to the point of the follicle becoming straight and thin enough to prevent the hair from reentering the skin.

During a series of treatments (approximately every 10 days, over a period of six months or longer), a patient would shave prior to visiting an electrologist, allowing enough time for the onset of the disease (three to seven days).

An electrologist would then treat only the causative follicles, relieving an individual from pain and discomfort. The destruction of the hair follicle is to be performed extremely carefully to prevent scarring on the surface of the skin.

The alloted time for all treatments could vary extensively because of the growth cycles of hair on various parts of the body. It is estimated that 20% of the body's hair follicles are dormant at any given time. Therefore, treatment can take as much as one year or even longer in difficult and extreme cases.

To begin the electrolysis process, the patient is asked to grasp the grounding device (30) with one hand. The hair connector or probe (28) in FIG. 1 is then inserted inside the distorted hair follicle (16) to be treated. Electrical current is transferred to the soft moist tissue (18) surrounding the hair (14) within the skin and body of the patient. From the moist tissue surrounding the hair, the current is directed downward to the base or anchor portion of the hair structure that is referred to as the papilla (17). It is this area of the hair follicle that contains the salt water content. Once the electrical current reaches the salt water content found in the hair follicle, the electrolysis process begins. Essentially the electrical current causes the salt (NaCl) and the water ($H_2O$) to break up into their constituent chemical elements. This produces sodium hydroxide (NaOH) which is highly caustic and which results in a decomposition process within the hair follicle enabling it to be extracted as shown in U.S. Pat. No. 5,026,369 assigned to Hubert L. Cole.

Invasive electrolysis treatment itself causes temporary swelling. Therefore, an electrologist should immediately use cataphoresis (a process which reduces swelling) on the treated area.

THEORY OF OPERATION

To further reduce swelling, a patient should wash face with soapy water (within 12 hours), reshave (with trimmers), and release any missed ingrown hairs with a needle or toothpick (within 48 hours) following treatment. Previously treated hairs in the lower neck area should especially be released because they have less of a tendency to spring out on their own. A patient should also attempt to get a full eight hours of sleep for the next two or three days.

Also, a very thin layer of a topical application (such as isopropyl alcohol, alphahydroxy acid, or combinations of corn starch, aloe vera, etc.) could be applied overnight to help reduce swelling. The topical application could be in the form of a gel, soap, shaving foam, solution, cream ointment, lotion, or stick ointment. Also, during treatment, a patient should maintain minimal growth of beard (no more than $\frac{1}{4}$ inch).

Extra hairs on the face tend to incubate the growth of germs which cause infection. The closer shaven a patient is, the quicker any pustules, papules, inflammation or swelling will go down; therefore, reducing the risk of prolonged infection. A patient is encouraged to shave with clippers or trimmers, since many straight razors cut hairs below the slain, resulting in intrafollicular ingrown hairs. While I believe extra hairs on the face tend to incubate the growth of germs which cause infection, I do not wish to be bound by this. However, it is known that prolonged infection of any area of the slain could possibly lead to damaged tissue.

If necessary, at the very end of all treatments, a patient could receive monthly cortizone injections (such as Kenalog manufactured by Squibb of Buffalo, N.Y.), to reduce the size of any preexisting scar tissue caused by ingrown hairs or other infections. A patient should wait five to seven weeks before the injections to allow the hairs of treated follicles a chance to resurface. For the first three days following injections, a patient should receive a full eight hours sleep. This inventive method of treatment has been tested on a limited basis and the results have been positive.

The method, preparation, and process of the present invention may be used in the treatment (i.e., alleviation of conditions and effects) of pseudofolliculitis barbae to prevent or, at the least, minimize the recurrence of the condition, as evidence of the foregoing test.

CONCLUSION, RAMIFICATIONS, AND SCOPE OF INVENTION

Although the above description contains many specificities, these should not be construed as limitations on the scope of the invention but, rather, as an exemplification of one preferred embodiment thereof. Many other variations are possible. For example, several different types of topical applications and shaving devices could be used in many different combinations during the inventive process and method. Furthermore, there could also be several variations in the different types of electrolysis apparatus and the different techniques used such as direct current, thermolysis and blend methods. There could also be time variations in all of the processes and methods of the current invention. Also, prior to treatment, a patient could seek medical advice from a dermatologist concerning the condition of their skin being subjected to electrolysis. Accordingly, the scope of the invention should be determined not by the embodiments illustrated but by the appended claims and their legal equivalents.

I claim:

1. A method for treating pseudofolliculitis barbae, comprising the following steps:
   a. shaving an area of a patient to be treated,
   b. waiting a sufficient period of time after shaving to allow ingrowth of hair follicles which indicates an onset of pseudofolliculitis barbae,
   c. identifying an ingrown hair follicle which is causative of pseudofolliculitis barbae, said ingrown hair follicle containing an ingrown hair,
   d. applying a permanent hair removal method for extracting said ingrown hair from said ingrown hair follicle,
   e. repeating steps c and d until all ingrown hairs associated with hair follicles identifiable as ingrown have been extracted.

2. The method of claim 1 wherein step b comprises waiting a period of approximately three to seven days after shaving to allow ingrowth of hair follicles which indicates an onset of pseudofolliculitis barbae.

3. The method of claim 1 further comprising the step of:
   f. waiting a delay period between treatments and repeating steps a through e for any recurring or newly ingrown hair follicles.

4. The method of claim 1 further comprising the step of:
   f. waiting a delay period of approximately ten days between treatments and repeating steps a through e for any recurring or newly ingrown hair follicles.

5. The method of claim 1 wherein said permanent hair removal method of step d comprises an electrolysis process, including the following steps:
   f. providing a source of electrical energy for electrolysis, said source of electrical energy for electrolysis comprising an electrical grounding device and a probe,
   g. electrically connecting the patient to said electrical grounding device, 6. The method of claim 5 wherein said ingrown hair within said ingrown hair follicle comprises a papilla and wherein step i comprises the substep of applying said electrical energy through said probe directly to said papilla.

7. The method of claim 5 wherein step i comprises the substep of applying said electrical energy from said source of electrical energy for electrolysis through said probe to said ingrown hair follicle as a direct current.

8. The method of claim 5 wherein step i comprises the substep of applying said electrical energy from said source of electrical energy for electrolysis through said probe to said ingrown hair follicle as an alternating current.

9. The method of claim 5 wherein step i comprises the substep of applying said electrical energy from said source of electrical energy for electrolysis through said probe to said ingrown hair follicle as a high frequency sinusoidal alternating current.

10. The method of claim 5 wherein step i comprises the substep of applying said electrical energy from said source of electrical energy for electrolysis through said probe to said ingrown hair follicle as a combination of direct current and high frequency sinusoidal alternating current.

11. A method for treating pseudofolliculitis barbae, comprising the following steps:
    a. shaving an area of a patient to be treated,
    b. waiting a period of time of approximately three to seven days after shaving which is sufficient to allow ingrowth of hair follicles which indicates an onset of pseudofolliculitis barbae in the area previously shaved,
    c. identifying art ingrown hair follicle which is causative of pseudofolliculitis barbae, said ingrown hair follicle containing an ingrown hair,
    d. applying an electrolysis process for extracting said ingrown hair from said ingrown hair follicle,
    e. repeating steps c and d until all ingrown hairs associated with hair follicles identifiable as ingrown have been extracted,
    f. waiting a delay period between treatments and repeating steps a through e at an interval of approximately ten days for any recurring or newly ingrown hair follicles,
    g. repeating steps a through f until no significant signs of pseudofolliculitis barbae are identified in steps b and c.
    h. inserting said probe into said ingrown hair follicle,
    i. applying electrical energy from said source of electrical energy through said probe to said ingrown hair follicle for a sufficient time to allow extraction of said ingrown hair from said ingrown hair follicle,
    j. extracting said ingrown hair from said ingrown hair follicle.

12. The method of claim 11 wherein the electrolysis process of step d comprises the following steps:
    h. providing a source of electrical energy for electrolysis, said source of electrical energy for electrolysis comprising an electrical grounding device and an electrical probe,
    i. electrically connecting the patient to said electrical grounding device,
    j. inserting said electrical probe into said ingrown hair follicle,
    k. applying electrical energy from said source of electrical energy through said electrical probe to said ingrown hair follicle for a sufficient time to allow extraction of said ingrown hair from said ingrown hair follicle,
    l. extracting said ingrown hair from said ingrown hair follicle.

13. The method of claim 12 wherein step k comprises the substep of applying said electrical energy from said source of electrical energy for electrolysis through said probe to said ingrown hair follicle as a direct current.

14. The method of claim 12 wherein step k comprises the substep of applying said electrical energy from said source of electrical energy for electrolysis through said probe to said ingrown hair follicle as an alternating current.

15. The method of claim 12 wherein step k comprises the substep of applying said electrical energy from said source of electrical energy for electrolysis through said probe to said ingrown hair follicle as a high frequency sinusoidal alternating current.

16. The method of claim 12 wherein step k comprises the substep of applying said electrical energy from said source of electrical energy for electrolysis through said probe to said ingrown hair follicle as a combination of direct current and high frequency sinusoidal alternating current.

* * * * *

UNITED STATES PATENT AND TRADEMARK OFFICE
CERTIFICATE OF CORRECTION

PATENT NO. : 5,419,344

DATED : May 30, 1995

INVENTOR(S) : Thomas Lee Dewitt

It is certified that error appears in the above-indentified patent and that said Letters Patent is hereby corrected as shown below:

On the title page, in the Abstract, line 26, change "or" to --of--.

Column 3, line 16, change "ache" to --acne--.

Column 6, lines 26 and 30, change "slain" to --skin--.

Column 6, line 32, after "necessary," change "at the very end of all treatments, a patient could receive monthly cortizone injections" to --a patient could receive cortizone injections approximately every three weeks--.

Signed and Sealed this

Twenty-sixth Day of September, 1995

Attest:

BRUCE LEHMAN

*Attesting Officer*     *Commissioner of Patents and Trademarks*